United States Patent [19]

Steinmeyer

[11] Patent Number: 5,008,909
[45] Date of Patent: Apr. 16, 1991

[54] DIFFRACTOMETER DATA COLLECTING METHOD AND APPARATUS

[75] Inventor: Peter A. Steinmeyer, Farmington, N. Mex.

[73] Assignee: The United States of America as represented by the Department of Energy, Washington, D.C.

[21] Appl. No.: 476,184

[22] Filed: Feb. 7, 1990

[51] Int. Cl.$^5$ .......................................... G01N 23/20
[52] U.S. Cl. ...................................... 378/71; 378/72; 378/73
[58] Field of Search ............... 378/71, 72, 73, 81, 378/83, 86–89; 250/390.09

[56] References Cited

U.S. PATENT DOCUMENTS

| | | | |
|---|---|---|---|
| 2,558,492 | 6/1951 | Lely et al. | 250/105 |
| 3,327,114 | 6/1967 | Diorio et al. | 250/51.5 |
| 3,411,000 | 11/1968 | Schliephake et al. | 250/51.5 |
| 3,852,594 | 12/1974 | Paolini | 250/278 |
| 4,140,904 | 2/1979 | Poot et al. | 250/272 |
| 4,541,107 | 9/1985 | Rossi | 378/146 |
| 4,562,585 | 12/1985 | Göbel et al. | 378/49 |
| 4,696,024 | 9/1987 | Pesch | 378/73 |

Primary Examiner—Carolyn E. Fields
Assistant Examiner—David P. Porta
Attorney, Agent, or Firm—Anne D. Daniel; James H. Chafin; William R. Moser

[57] ABSTRACT

Diffractometer data is collected without the use of a movable receiving slit. A scanning device, positioned in the diffractometer between a sample and detector, varies the amount of the beam diffracted from the sample that is received by the detector in such a manner that the beam is detected in an integrated form. In one embodiment, a variable diameter beam stop is used which comprises a drop of mercury captured between a pair of spaced sheets and disposed in the path of the diffracted beam. By varying the spacing between the sheets, the diameter of the mercury drop is varied. In another embodiment, an adjustable iris diaphragm is positioned in the path of the diffracted beam and the iris opening is adjusted to control the amount of the beam reaching the detector.

16 Claims, 2 Drawing Sheets

DIFFRACTOMETER DATA COLLECTING METHOD AND APPARATUS

The United States Government has rights in this invention pursuant to Contract No. DE-AC04-76DP03533 awarded by the U.S. Department of Energy to Rockwell International Corp.

FIELD OF THE INVENTION

The present invention relates to diffractometers and, more particularly, to an improved method and apparatus for collecting diffraction data.

BACKGROUND ART

Data produced by X-ray diffractometers is conventionally collected using a moving receiving slit. In the mostly commonly used mode of diffraction data collection, step scanning is employed to determine the spatial distribution of the radiation intensity (also referred to as the the so-called 2Θ profile, wherein Θ is the Bragg angle) and the receiving slit is moved to a new value of 2Θ for each step of the scanning operation, with the number of X-ray counts being measured and recorded for each step. In a variation of this method, Debye-Scherrer X-ray optics are used, particularly in microdiffractometer instruments. In Debye-Sherrer arrangements, the 2Θ scanning is provided by moving an annular receiving slit along the axis of the diffractometer. As will be appreciated, the need to move a receiving slit places a number of limitations on prior art diffractometers, including problems of alignment and tracking, and adds to the general overall complexity of the instrument.

Diffractometers in general, and diffractometers which employ moving receiving slits in particular, are fully described in the literature. Patents of possible interest insofar as the present invention is concerned include the following U.S. Pat. Nos. 4,696,024 (Pesch); 4,140,904 (Poot, et al.); 3,411,000 (Schliephake, et al.); 3,852,594 (Paolini); and 3,327,114 (Diorio, et al.). Briefly considering these patents, the Pesch Patent discloses a gamma diffractometer device used in studying imperfections in single crystals. A conventional scanning method is employed wherein the Bragg angle is varied and the diffracted radiation beams (gamma rays) are admitted to a radiation detector through a shutter operated receiving slit or slot. The Schliephake, et al. patent discloses a diffractometer accessory for controlling the width of an incident X-ray beam falling on a sample during scanning of a conventional X-ray diffractometer. The Paolini patent discloses a similar device. The Poot, et al. patant discloses a Debeye camera for powder samples which is capable of providing multiple samples on a single sheet of X-ray film. The Diorio patent discloses a low angle X-ray scattering device using a collimating arrangement, ccmprising series of apertures, for reducing the angular divergence of a primary X-ray beam.

SUMMARY OF THE INVENTION

In accordance with the invention, a method and apparatus are provided for collecting diffractometer data without using a movable receiving slit. As a consequence of this, a diffractometer incorporating the invention is both simple and versatile, making such a diffractometer useful in virtually any analysis laboratory. In contrast to conventional moving slit scanning systems the invention presents little difficulty insofar as alignment and tracking are concerned. Further, the small width of the scanning apparatus permits the diffractometer to be disposed very close to the sample under test, resulting in a gain in fluorescent intensity as compared with prior art systems. This close positioning of the diffractometer relative to the sample permits the resultant instrument to be used for elemental analysis so that diffraction data and fluorescence data can be simultaneously gathered or collected with the same stand-alone instrument, thereby making the instrument useful in a number of different applications.

According to a first aspect of the invention, an improvement is provided in a diffractometer comprising means for producing a primary beam, a sample holder for suspending a sample in the path of the primary beam, and a detector means for detecting the diffracted beam produced when the primary beam strikes the sample, wherein the improvement comprises scanning means disposed at a fixed location between said holder and said detector means for varying the total amount of the cross sectional area of the diffracted beam that is received by the detector means in a manner such that the diffracted beam is detected in an integrated form.

In one preferred embodiment, the scanning means comprises adjustable blocking means disposed in the path of the diffracted team so as to block a variable portion thereof from reaching the detector means, and means for varying the size of the blocking means so as to vary the amount of the diffracted beam reaching the detector means. The adjustable blocking means preferably comprises a variable diameter beam stop. Advantageously, the variable daimeter team stop comprises a pair of spaced, parallel sheets having a drop of mercury captured therebetween, and spacing adjustment means for varying the spacing between the sheets so as to vary the diameter of the drop of mercury. The spacing adjustment means preferably comprises a plurality of synchronously operated micrometers. Advantageously, there is further provided spring means for biasing one sheet of the pair of sheets towards engagement with the other sheet.

In a second preferred embodiment, the scanning means comprises means defining an opening of adjustable size disposed in the path of the diffracted beam and means for adjusting the size of said opening so as to vary the amount of the diffracted team that passes therethrough. Preferably, the scanning means comprises an adjustable iris diaphragm providing a variable diameter opening.

In accordance with a further aspect of the invention, a method is provided for collecting diffraction data from a diffracted beam in a diffractometer system including a detector which receives the diffracted beam, the method comprising scanning the diffracted beam by blocking a varying amount of cross section ofthe diffracted beam which is received by the detector in such a manner that the diffracted team is detected in an integrated form.

In one embodiment of the method, blocking a variable amount of the diffracted team is achieved by varying the size of an opening through the beam that passes. Preferably, the opening comprises the iris opening provided by an iris diaphragm as discussed above, and varying the size of the opening comprises incrementally adjusting the diameter of the iris opening.

In a further embodiment of this method, blocking a variable amount of the beam is achieved by varying the size of beam stop positioned in the path of the diffracted beam. Preferably, the beam stop comprises a drop of mercury as discussed above, and varying the size of beam stop comprises varying the diameter of the drop of mercury. Advantageously, as was also discussed hereinabove, the drop of mercury is captured between two metal sheets and varying the diameter of the drop of mercury is effected by varying the spacing between the sheets. In accordance with a further aspect of the invention, the detector comprises an energy selective detector and the method of the invention further comprises performing an elemental analysis of the sample using the detector, as discussed above. Preferably, scanning is carried out in steps, the detector counts for a predetermined count the time during the steps, and the data for the elemental analysis and data collected from scanning of the diffracted beam are collected during alternating periods of the count time of the detector for each scanning step.

Other features and advantages of the invention will be set forth in, or apparent from, the detailed description of preferred embodiments of the invention which follows.

DESCRIPTION OF THE PREFERRED EMBODIMENTS

Figure 1:
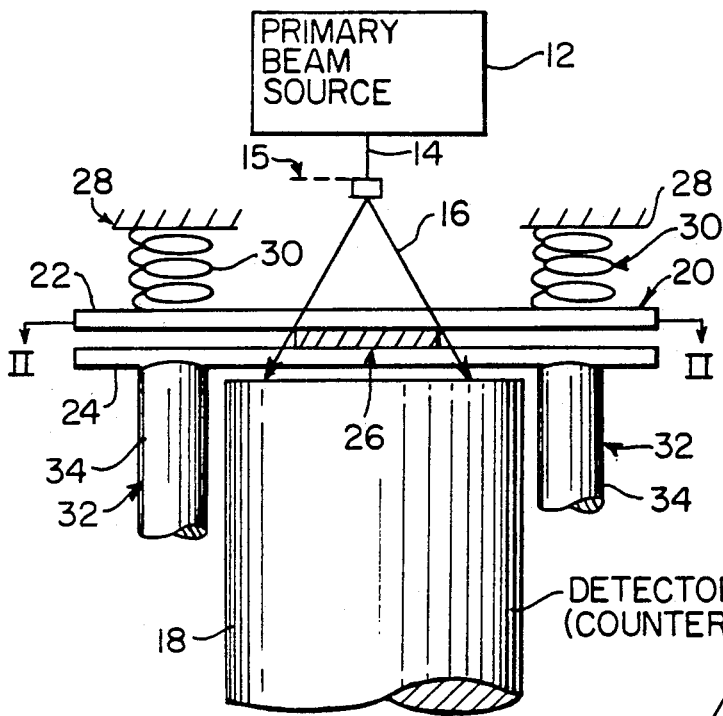
FIG. 1 is a highly schematic side elevational view of a diffractometer incorporating a scanning apparatus in accordance with a first embodiment of the invention.
Figure 2:
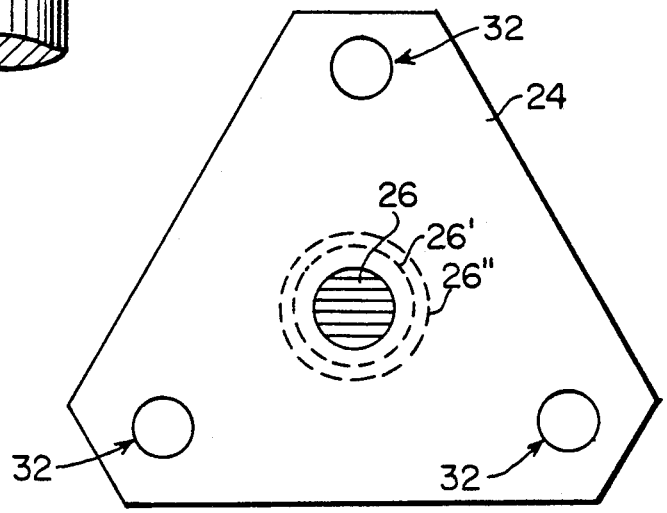
FIG. 2 is a simplified cross sectional view taken generally along line II—II of FIG. 1.

Referring to FIGS. 1 and 2, there are shown the basic components of an integral scanning diffractometer in accordance with a preferred embodiment of the invention. As shown in FIG. 1, a primary beam 10 from a beam source 12 is directed toward a sample 14, held by a sample holder indicated schematically at 15, and the diffracted beam 16 is detected by a detector (counter) 18 which, in the specific exemplary embodiment being considered, comprises a pulse height analyser. As stated above, the scanning apparatus of the invention is applicable to many different types of conventional diffractometers and because the construction and operation of such diffractometers are well known and form no part of the invention, further description of the diffractometer, apart from the scanning appratus of the invention, will be dispensed with.

In the embodiment of FIGS. 1 and 2, the scanning apparatus, which is denoted 20, takes the form of a variable diameter beam stop comprising a pair of sheets or plates 22 and 24, made of beryllium or the like, having a drop of mercury, indicated at 26, captured therebetween. Plates 22 and 24 are mounted in spaced parallel relationship, separated only by the thickness of the drop of mercury 26, with upper plate 22 being suspended from a support or supports 28 by compression springs 30 which bias plate 22 towards plate 24. Plates 22 and 24 are both generally triangular in shape as shown in FIG. 2 for plate 24. Plate 24 is mounted by three micrometers 32 the shafts 34 of which are shown in FIG. 1. The micrometers 32 are synchronously operated so as to be adjusted in parallel and thus provide movement of plate 24 parallel to plate 22, toward and away therefrom. As will be understood, and as is illustrated in dashed lines in FIG. 2, such movement of plate 24 towards and away from plate 22 will vary the size of mercury drop 26 and thereby vary the amount of the diffracted team 16 which is blocked by mercury drop 26. More particularly, as sheet or plate 24 moves toward plate 22, the mercury drop 26 flattens and spreads out in a circular manner. Because mercury provides high attenuation of X-rays used in diffraction, the variable diameter mercury drop or spot 26 provides an integral diffraction scan when the diameter thereof is varied.

Figure 3:
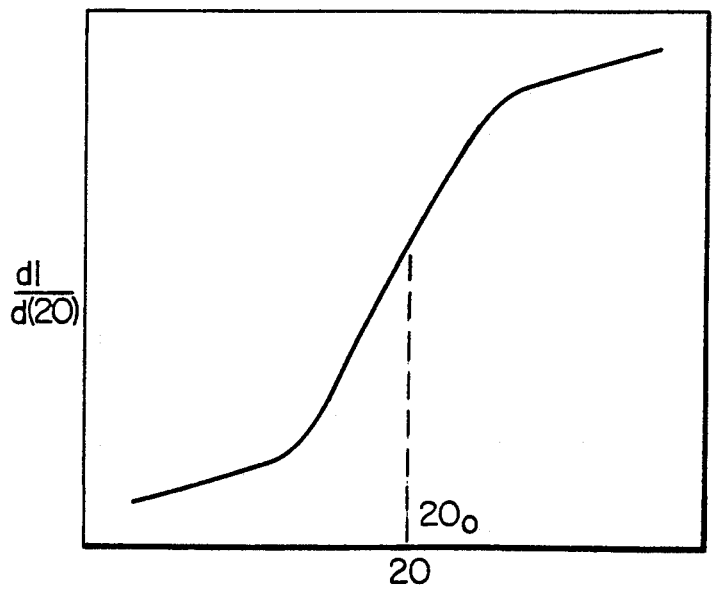
FIG. 3 is a representative plot of the intensity data or 2Θprofile produced by a diffractometer incorporating a scanning apparatus in accordance with the invention.
Figure 4:
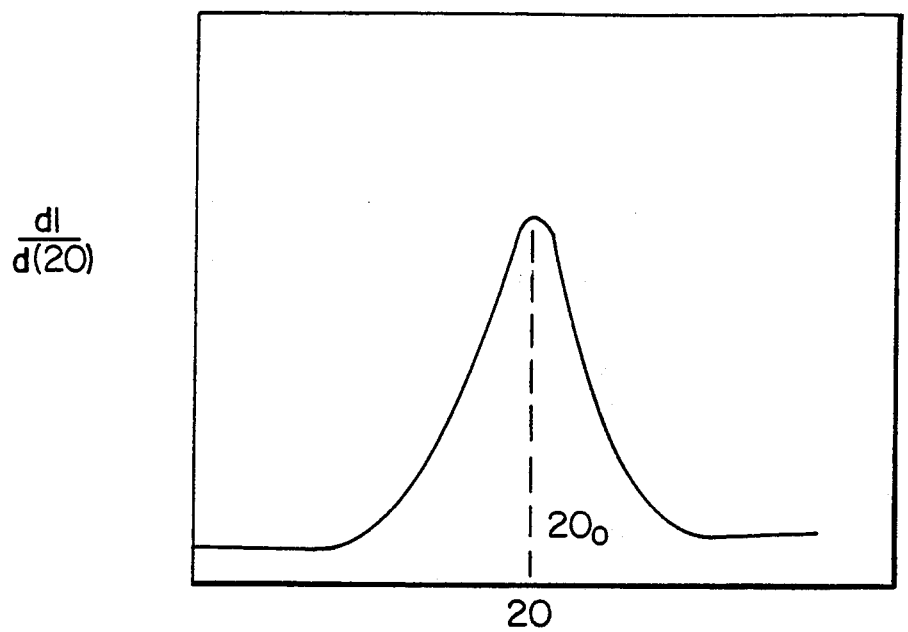
FIG. 4 is a plot of intensity data of FIG. 3 after differentiation thereof.

The intensity data produced by diffractometer constructed in accordance with the invention is shown in FIG. 3, wherein intensity is plotted against 2Θwhich is varied as described above. The trace produced is an integrated version of that which would be produced by a conventional moving receiving slit and thus must be differentiated as illustrated in FIG. 4 in order to show the position of the diffraction peak. If the data is taken in a step scan mode, i.e., in a mode wherein the diameter of the drop 26 is varied in discrete steps, the differentiation can be acccomplished using digital processing whereas if continuous scanning is used, the differentiation can be done using a conventional analog differentiation circuit.

As mentioned above, because of the samll width of the scanning apparatus, the detector 18 can be placed very close to the sample 16, there providing an increase in intensity as compared with a conventional moving slit. This increase in intensity enables the apparatus of the invention to be used for elemental analysis. In this regard, because of the close proximity of the sample 16 and the detector 18, fluorescent X-rays can also be detected if an energy-selective detector such as a pulse height analyzer is used. In such a situation, the pulse height analyzer (detector) 18 is operated in a baseline scan mode during the diffraction scan. In an illustrative example, the pulse height analyzer 18 is programmed to count the diffracted X-rays for 50 per cent of the count time at each 2Θstep while the other 50 per cent of the count is dedicated to a baseline sweep for other, (e.g., fluorescent) X-rays. Because the X-ray flux incident on the face of detector 18 is high, due, as explained above, to the relatively large opening and the short distance between the sample 16 and the detector 18, rapid diffraction and fluorescence analysis can be carried out simultaneously.

Figure 5:
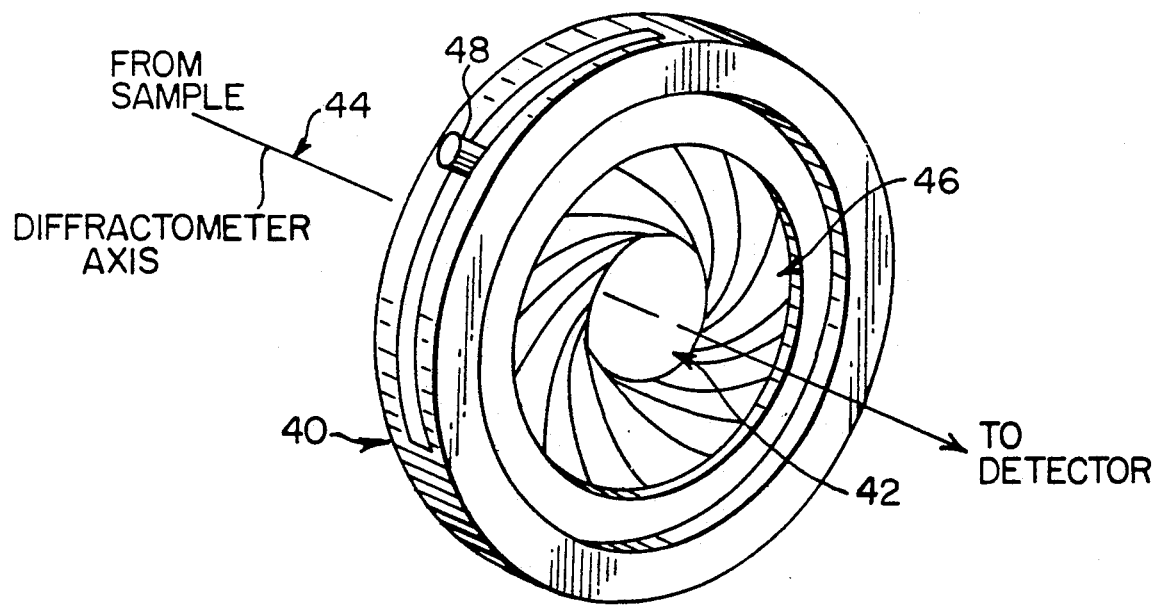
FIG. 5 is a perspective view of a second embodiment of a scanning apparatus constructed in accordance with the invention.

Referring to FIG. 5, a further embodiment of the invention is shown. In this embodiment, an iris diaphragm 40 is used to provide microdiffractometer scanning. The iris diaphragm 40 is positioned between the sample (not shown) and the detector (not shown) and disposed so that the center of the opening 42 is coincident with the diffractometer axis 44. Iris diaphragm 40 is conventional in construction and includes a plurality of leaves 46 the movement of which is controlled by an actuator 48 to vary the size of opening 42. In a preferred embodiment, the iris opening 42 is opened incrementally for integral scanning of the Debye rings.

Although the present invention has been described relative to exemplary embodiments thereof, it will be understood by those skilled in the art that variations and modifications can be effected in these exemplary embodiments without departing from the scope and spirit of the invention.

What is claimed is:

1. In a diffractometer comprising means for producing a primary beam, a sample holder for suspending a sample in the path of the primary beam, and a detector means for detecting a diffracted beam produced when the primary beam strikes the sample, the improvement comprising scanning means disposed at a fixed location between said holder and said detector means for varying the total amount of the cross sectional area of the diffracted team that is received by the detector means in a manner such that the diffracted beam is detected in an integrated form.

2. A diffractometer as claimed in claim 1 wherein said scanning means comprises adjustable blocking means disposed in the path of said diffracted beam so as to block a variable portion thereof from reaching said detector means and means, for varying the size of said blocking means so as to vary the amount of the diffracted beam reaching said detector means.

3. A diffractometer as claimed in claim 2 wherein said adjustable blocking means comprises a variable diameter beam stop.

4. A diffractometer as claimed in claim 3 wherein said variable diameter beam stop comprises a pair of spaced, parallel sheets having a drop of mercury captured therebetween, and spacing adjustment means for varying the spacing between the sheets so as to vary the diameter of the drop of mercury.

5. A diffractometer as claimed in claim 4 wherein said spacing adjustment means comprises a plurality of synchronously operated micrometers.

6. A diffractometer as claimed in claim 5 further comprising spring means for biasing one sheet of said pair of sheets towards engagement with the other sheet of said pair of sheets.

7. A diffractometer as claimed in claim 1 wherein said scanning means comprises means defining an opening of adjustable size disposed in the path of the diffracted beam and means for adjusting the size of said opening so as to vary the amount of the diffracted team that passes therethrough.

8. A diffractometer as claimed in claim 1 wherein said scanning means comprises an adjustable iris diaphragm providing a variable diameter opening.

9. A method for collecting diffraction data from a diffracted beam in a diffractometer system including a detector which receives the diffracted beam, said method comprising scanning the diffracted beam by blocking a varying amount of cross section of the diffracted team which is received by the detector in suuh a manner that the diffracted beam is detected in an integrated form.

10. A method for collecting diffraction data as claimed in claim 9 wherein blocking a variable amount of the diffracted beam is achieved by varying the size of an opening through which said beam passes.

11. A method for collecting diffraction data as claimed in claim 10 wherein said opening comprises an iris opening provided by an iris diaphragm and varying the size of said opening comprises incrementally adjusting the diameter of the iris opening.

12. A method for collecting diffraction data as claimed in claim 9 wherein blocking a variable amount of said beam is achieved by varying the size of a beam stop positioned in the path of the diffracted team.

13. A method for collecting diffraction data as claimed in claim 12 wherein said beam stop comprises a drop of mercury and varying the size of said beam stop comprises varying the diameter of the drop of mercury.

14. A method for collecting diffraction data as claimed in claim 13 wherein the drop of mercury is captured between two metal sheets and varying the diameter of the drop of mercury is effected by varying the spacing between the sheets.

15. A method for collecting diffraction data as claimed in claim 9 wherein said detector comprises an energy selective detector and said method further comprises performing an elemental analysis of a sample using said detector.

16. A method for collecting diffraction data as claimed in claim 15 wherein said scanning is carried out in steps, wherein said detector counts for a predetermined count time during said steps, and wherein data for the elemental analysis and data collected from scanning of the diffracted beam are collected during alternating periods of the count time of said detector for each scanning step.

* * * * *